(12) United States Patent
Hara et al.

(10) Patent No.: US 9,284,561 B2
(45) Date of Patent: Mar. 15, 2016

(54) TRANSFORMANT AND PROCESS FOR PRODUCTION THEREOF, AND PROCESS FOR PRODUCTION OF LACTIC ACID

(75) Inventors: Futoshi Hara, Tokyo (JP); Hideki Tohda, Tokyo (JP); Yuko Hama, Tokyo (JP); Chihiro Hama, legal representative, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 271 days.

(21) Appl. No.: 13/401,197

(22) Filed: Feb. 21, 2012

(65) Prior Publication Data
US 2012/0214214 A1    Aug. 23, 2012

Related U.S. Application Data

(63) Continuation of application No. PCT/JP2010/063888, filed on Aug. 17, 2010.

(30) Foreign Application Priority Data

Aug. 21, 2009    (JP) ................................ 2009-192271

(51) Int. Cl.
| | | |
|---|---|---|
| C12P 7/56 | (2006.01) | |
| C12N 1/00 | (2006.01) | |
| C12N 15/63 | (2006.01) | |
| C12N 15/52 | (2006.01) | |
| C12N 9/04 | (2006.01) | |

(52) U.S. Cl.
CPC .............. *C12N 15/52* (2013.01); *C12N 9/0006* (2013.01); *C12P 7/56* (2013.01)

(58) Field of Classification Search
None
See application file for complete search history.

(56) References Cited

U.S. PATENT DOCUMENTS

| | | |
|---|---|---|
| 6,429,006 B1 | 8/2002 | Porro et al. |
| 2003/0032152 A1 | 2/2003 | Porro et al. |
| 2003/0190630 A1 | 10/2003 | Rajgarhia et al. |
| 2005/0112737 A1 | 5/2005 | Liu et al. |
| 2006/0148050 A1 | 7/2006 | Porro et al. |
| 2007/0031950 A1 | 2/2007 | Winkler |
| 2008/0311583 A1* | 12/2008 | Hirashima et al. ................. 435/6 |
| 2009/0226991 A1* | 9/2009 | Feldman et al. .............. 435/160 |

FOREIGN PATENT DOCUMENTS

| | | |
|---|---|---|
| CN | 1902319 A | 1/2007 |
| JP | 05-015380 | 1/1993 |
| JP | 07-163373 | 6/1995 |
| JP | 10-234375 | 9/1998 |
| JP | 2000-262284 | 9/2000 |
| JP | 2001-204464 | 7/2001 |
| JP | 2001-516584 A | 10/2001 |
| JP | 2005-198612 | 7/2005 |
| JP | 2006-006271 | 1/2006 |
| JP | 2007-512018 A | 5/2007 |
| JP | 2008-048726 | 3/2008 |
| WO | WO-95/09914 | 4/1995 |
| WO | WO-99/14335 | 3/1999 |
| WO | WO-99/23223 | 5/1999 |
| WO | WO-02/101038 A1 | 12/2002 |
| WO | WO 2004/099425 A2 | 11/2004 |
| WO | WO-2005/052174 A2 | 6/2005 |
| WO | WO-2007/015470 A1 | 2/2007 |
| WO | WO-2007/063919 A1 | 6/2007 |

OTHER PUBLICATIONS

GenPept Accession No. NP_592796, May 2008, 2 pages.*
GenPept Accession No. XP_001713041, May 2008, 2 pages.*
GenPept Accession No. NP_595027, May 2008, 2 pages.*
GenPept Accession No. NP_594083, May 2008, 2 pages.*
Hoff et al., Mol. Cell. Biol. 18:6839-6852, 1998.*
Blalock et al., "Expression of Pyruvate Decarboxylase in a Gram Positive Host: Sarcina ventriculi Pyruvate Decarboxylase Versus Other Known Pyruvate Decarboxylases", Dissertation, University of Florida, 2003.*
Sasaki et al., Nucleic Acids Res. 41:5382-5399, 2013.*
Bianchi, M et al. "Efficient Homolactic Fermentation by *Kluyveromyces* lactis Strains Defective in Pyruvate Utilization and Transformed with the Heterologous LDH Gene", Applied and Environmental Microbiology, Dec. 2001, vol. 67, No. 12, pp. 5621-5625.
Ikushima S., et al. "Genetic Engineering of *Candida utilis* yeast for Efficient Production of $_L$-Lactic Acid", Biosci. Biotechnol. Biochem, 2009, vol. 73, No. 8, pp. 1818-1824.
International Search Report in PCT/JP2010/063888 dated Sep. 28, 2010.
Ishida, N. et al. "The Effect of Pyruvate Decarboxylase Gene Kockout in *Saccharomyces cerevisiae* on L-Lactic Acid Production", Biosci. Biotechnol. Biochem., 2006, vol. 70, No. 5, pp. 1148-1153.
Wood, V. et al. "The genome sequence of Schizosaccharomyces pombe", Nature, Feb. 21, 2002, vol. 415, No. 6874, pp. 871-880.
Hara, F. et al. "Bunretsu Kobo o Mochiita Muchuwa deno L-Nyusan Seisan ni Okeru Taisha Seigyo", Annual Meeting of the Molecular Biology Society of Japan Program Koen Yoshishu, Nov. 20, 2009, vol. 32, p. 263 [3P-0890].
Hara, F. et al. "Lactate production using *Schizosaccharomyces pombe*", Abstracts of the Annual Meeting of the Society for Biotechnology, Japan, 2008, vol. 60, p. 135 [1Ep10].
Hara, F. et al. "Lactate production using *Schizosaccharomyces pombe*", Abstracts of the Annual Meeting of the Society for Biotechnology, Japan, Aug. 25, 2009, vol. 61, p. 190 [2Mp08].

(Continued)

*Primary Examiner* — David J Steadman
(74) *Attorney, Agent, or Firm* — Foley & Lardner LLP

(57) ABSTRACT

The present invention relates to a transformant, containing a lactate dehydrogenase gene which is introduced into *Schizosaccharomyces pombe* as a host, in which a part of a gene cluster encoding a pyruvate decarboxylase in the *Schizosaccharomyces pombe* host is deleted or inactivated.

14 Claims, No Drawings

(56) References Cited

OTHER PUBLICATIONS

Sakurai, M. et al. "Bunretsu Kobo no Alcohol Dehydrogenase Idenshi Hakai Kabu ni Okeru Totaisha no Kaiseki", the 26th Annual Meeting of the Molecular Biology Society of Japan Program Koen Yoshishu, 2003, vol. 26, p. 609 [1PA-421].

Supplementary European Search Report EP 10809970.6 dated Mar. 4, 2013.

Stefan Hohmann, "Characterisation of *PDC2*, a gene necessary for high level expression of pyruvate decarboxylase structural genes in *Saccharomyces cereyisiae*", Mol. Gen. Genet. (1993) 241:657-666.

Nathan J. Bowen et al., "Retrotransposons and Their Recognition of pol II Promoters: A Comprehensive Survey of the Transposable Elements From the Complete Genome Sequence of *Schizosaccharomyces pombe*", Genome Research, pp. 1984-1997, 2003, vol. 13, No. 9.

Hirashima, et al. "A simple and effective chromosome modification method for large-scale deletion of genome sequences and identification of essential genes in fisson yeast,"Nucleic Acids Research, vol. 34, No. 2, 2006, pp. 2-8.

* cited by examiner

TRANSFORMANT AND PROCESS FOR PRODUCTION THEREOF, AND PROCESS FOR PRODUCTION OF LACTIC ACID

TECHNICAL FIELD

The present invention relates to a transformant and a process for production thereof, and a process for production of lactic acid.

BACKGROUND ART

Lactic acid is broadly used in chemical raw materials such as of medical treatments, and cosmetics. Also, polylactic acid which is obtained by using lactic acid is drawing attention as a biodegradable plastic which is degraded finally into carbon dioxide and water by a microorganism and the like. Because of this, it is necessary to produce lactic acid with a low cost and a high productivity.

As the method for producing lactic acid, there is known a biological method in which it is produced by fermenting a sugar by a lactic acid bacterium. However, since lactic acid bacteria have low acid resistance, in order to obtain a high productivity by this method, it is necessary to convert the lactic acid produced by the fermentation into a lactic acid salt by neutralizing it with an alkali. Since such neutralization with an alkali requires a step for restoring lactic acid from the lactic acid salt, the production process becomes complex and the production cost also becomes high.

Accordingly, as the method for obtaining lactic acid without carrying out neutralization with an alkali, there have been shown a method which uses a transformant containing an acid resistant microorganism such as a yeast belonging to the genus *Saccharomyces* as a host and prepared by introducing a gene encoding a lactate dehydrogenase into the acid resistant microorganism (Patent Reference 1); and a method which uses *Saccharomyces cerevisiae* (budding yeast) into which a gene encoding a lactate dehydrogenase was introduced and in which a gene encoding a pyruvate decarboxylase 1 was deleted or inactivated (Patent Reference 2).

RELATED ART REFERENCES

Patent References

Patent Reference 1: JP-A-2001-204464
Patent Reference 2: JP-A-2008-48726

SUMMARY OF THE INVENTION

Problems that the Invention is to Solve

However, the method of Patent Reference 1 can provide merely from 2% to 5% of lactic acid even by a culturing time of from 20 hours to 24 hours so that the productivity is not sufficient. Also, the method of Patent Reference 2 is not suited for the industrial mass production of lactic acid because it becomes necessary to carry out neutralization with an alkali when lactic acid is produced in a large amount. Thus, a method which can produce lactic acid with a high productivity without carrying out neutralization with an alkali is in demand.

Accordingly, an object of the present invention is a transformant of *Schizosaccharomyces pombe* which can produce lactic acid with a high productivity without requiring neutralization with an alkali and a method for producing the transformant. Further object is a transformant which is suited for the production of lactic acid under the presence of a high concentration of a sugar and is also suited for high density fermentation, and a method for producing the transformant.

In addition, another object is a method for producing lactic acid with a high productivity without carrying out the neutralization step with an alkali, using the aforementioned transformant.

In this connection, the lactic acid according to the present invention means L-lactic acid which is obtained by a biological method.

Means for Solving the Problems

The transformant according to the present invention comprises a lactate dehydrogenase gene which is introduced into *Schizosaccharomyces pombe* as a host, wherein a part of a gene cluster encoding a pyruvate decarboxylase in the *Schizosaccharomyces pombe* host is deleted or inactivated.

Moreover, in the transformant according to the present invention, the gene encoding a pyruvate decarboxylase which is deleted or inactivated is preferably PDC 2 gene. The lactate dehydrogenase gene is preferably a mammalian lactate dehydrogenase gene. Furthermore, the lactate dehydrogenase gene is preferably introduced into a chromosome of *Schizosaccharomyces pombe*.

Further, the method for producing a transformant according to the present invention is a method for producing a transformant comprising a lactate dehydrogenase gene in which a part of a gene cluster encoding a pyruvate decarboxylase is deleted or inactivated, containing: introducing an expression cassette into a host, by using *Schizosaccharomyces pombe* as the host and using a vector having the expression cassette that contains a promoter, a terminator and a lactate dehydrogenase gene functioning in *Schizosaccharomyces pombe* to obtain a transformant; and using, as the host, a host in which a part of a gene cluster encoding a pyruvate decarboxylase is deleted or inactivated, or deleting or inactivating a part of a gene cluster encoding a pyruvate decarboxylase of the obtained transformant.

Moreover, it is preferred that the vector further has a recombination region for carrying out a homologous recombination for a chromosome of *Schizosaccharomyces pombe*, and the expression cassette is introduced into the chromosome of *Schizosaccharomyces pombe* using this vector. Further, the target region where the homologous recombination is carried out in the chromosome of the host is preferably a transposon gene Tf2.

Furthermore, in the method of the present invention, the gene encoding a pyruvate decarboxylase which is deleted or inactivated is preferably PDC 2 gene. The lactate dehydrogenase gene is preferably a mammalian lactate dehydrogenase gene.

Further, the present invention relates to a method for producing lactic acid, which comprises culturing the above transformant in culture and obtaining lactic acid from the culture.

Moreover, in this method for producing lactic acid, the culturing is preferably carried out using a culture containing from 1% by mass to 50% by mass (further preferably, from 2% by mass to 16% by mass) in concentration of glucose. Furthermore, the culturing is preferably continued further after pH of the culture becomes 3.5 or less due to the lactic acid produced by the transformant.

Furthermore, initial cell density of the transformant in the culture is preferably set to from 0.1 g to 50 g (on the dry cell basis)/L (further preferably, from 0.2 g to 40 g (on the dry cell basis)/L). Further, the culturing is preferably continued without neutralizing lactic acid in the culture produced by the transformant. And lactic acid is preferably separated from the culture without neutralizing lactic acid in the culture produced by the transformant.

Advantage of the Invention

The transformant of *Schizosaccharomyces pombe* according to the present invention can produce lactic acid with a high productivity without requiring neutralization with an alkali. In addition, it is suited for the production of lactic acid in the presence of high concentration of sugars, particularly glucose, fructose, sucrose and maltose, and is also suited for a high density culturing. Further, by the transformant production method of the present invention, the transformant can be obtained conveniently.

In addition, the lactic acid production method of the present invention can produce lactic acid with a high productivity without carrying out a neutralization step with an alkali.

MODE FOR CARRYING OUT THE INVENTION

[Transformant]

The transformant of the present invention is a transformant which contains *Schizosaccharomyces pombe* (to be referred sometimes to as *S. pombe* hereinafter) as a host, in which a lactate dehydrogenase gene is introduced therein and a part of the gene cluster encoding a pyruvate decarboxylase in the *S. pombe* host is deleted or inactivated.

<*S. pombe*>

*S. pombe* as the host is a species of yeast belonging to the genus *Schizosaccharomyces* (fission yeast) and is a microorganism which is particularly excellent in acid resistance in comparison with other yeasts. The present inventors have found that *S. pombe* is excellent in the productivity of lactic acid under a high concentration of glucose and is also suited for a high density culturing (culturing using a large amount of yeast), in comparison with other yeasts such as *Saccharomyces cerevisiae* and found that lactic acid can be produced with a markedly high productivity by the use of a transformant of *S. pombe*.

In this connection, entire base sequence of *S. pombe* chromosome is recorded and opened to the public in the data base "GeneDB" of Sanger Institute as "*Schizosaccharomyces pombe* Gene DB (genedb.org/genedb/*pombe*/)". Sequence data of the *S. pombe* gene described in this specification can be obtained by retrieving from the above-mentioned data base by the gene name and the above-mentioned systemic name.

The *S. pombe* to be used in the present invention is not particularly limited with the proviso that it has acid resistance.

*S. pombe* can be obtained from a public or private depositary organization such as American Type Culture Collection (ATCC, Manassas, Va., USA), National Collection of Yeast Cultures (NCYC, Norwich, United Kingdom), NITE Biological Resource Center (NBRC, Kisarazu, Chiba, Japan), Yeast genetic Resource Center (YGRC, Science Research Course, Graduate School, Osaka City University, Japan) and the like.

<A Gene Cluster Encoding Pyruvate Decarboxylase>

There are 4 kind of groups in the gene encoding pyruvate decarboxylase (pyruvate decarboxylase gene, to be referred also to as "PDC gene" hereinafter) in *S. pombe*, namely a gene encoding pyruvate decarboxylase 1 (to be referred to as "PDC 1 gene" hereinafter), a gene encoding pyruvate decarboxylase 2 (to be referred to as "PDC 2 gene" hereinafter), a gene encoding pyruvate decarboxylase 3 (to be referred to as "PDC 3 gene" hereinafter), and a gene encoding pyruvate decarboxylase 4 (to be referred to as "PDC 4 gene" hereinafter). Particularly, PDC 2 gene and PDC 4 gene are the PDC genes which show main functions in *S. pombe*. Systemic names of the respective PDC genes are as follows.

PDC 1 gene (Pdc 1): SPAC13A11.06
PDC 2 gene (Pdc 2): SPAC1F8.07c
PDC 3 gene (Pdc 3): SPAC186.09
PDC 4 gene (Pdc 4): SPAC3G9.11c Sequence data of the above-mentioned PDC genes can be obtained by retrieving from the aforementioned *S. pombe* gene data base by the gene names and systemic names.

In the case of wild type *S. pombe*, the ethanol fermentation is carried out through a cycle in which glucose is metabolized into pyruvic acid by the glycolytic pathway, the pyruvic acid is converted into acetaldehyde by the pyruvate decarboxylase expressed from the aforementioned PDC gene and then the acetaldehyde is converted into ethanol by an alcohol dehydrogenase. In addition, since the wild type *S. pombe* does not have a functionable lactate dehydrogenase gene, a route for forming lactic acid from pyruvic acid is not present therein.

On the other hand, the lactate dehydrogenase expressed from the introduced lactate dehydrogenase gene produces lactic acid by reducing pyruvic acid to lactic acid. Accordingly, even when the wild type *S. pombe* is enabled to produce lactic acid by introducing a lactate dehydrogenase gene therein, the productivity of lactic acid does not become sufficiently high because both of the ethanol fermentation and lactic acid fermentation are carried out if it is as such.

The transformant of the present invention has a chromosome wherein a part of the aforementioned gene cluster encoding pyruvate decarboxylase is deleted or inactivated. By the deletion or inactivation of a part of PDC genes of the transformant, productivity of lactic acid is improved because the efficiency of ethanol fermentation of the transformant is lowered and the amount of pyruvic acid to be converted into ethanol is reduced. However, when the PDC genes are completely deleted or inactivated, the growth is inhibited because the ethanol fermentation cannot be carried out at all, so that those which are deleted or inactivated are limited to a part of the PDC genes.

It is particularly preferable that the PDC gene to be deleted or inactivated is the PDC 2 gene. The PDC 2 gene is a PDC gene which has a particularly main function.

As described in the foregoing, when the PDC genes are completely deleted or inactivated, the growth of the transformant is inhibited because it cannot carry out the ethanol fermentation. Accordingly, deletion or inactivation of the PDC genes must be carried out in such a manner that an ethanol fermentation capacity necessary for the growth is maintained so that sufficient amount of the transformant can be obtained and also that the ethanol fermentation capacity is lowered so that the fermentation efficiency of lactic acid is improved. The present inventors have carried out an examination on this problem and found as a result that the PDC 4 gene is activated to a certain degree when the PDC 2 gene is deleted or inactivated, so that a certain degree of the ethanol fermentation capacity by which sufficient amount of the transformant can be obtained can become compatible with the production of lactic acid at a high fermentation efficiency.

Deletion or inactivation of PDC gene can be carried out by a conventionally known method. For example, a PDC gene can be deleted by using the Latour method (described in Nucleic Acids Res., 2006, vol. 34, p. e11, International Publication No. 2007/063919, and the like).

In addition, the PDC gene can be inactivated by causing deletion, insertion, substitution or addition in a part of the base sequence of the PDC gene. Regarding these mutations by deletion, insertion, substitution or addition, only one of them may be conducted or two or more thereof may be conducted.

Regarding the method for introducing the aforementioned mutation into a part of the PDC gene, a conventionally known method can be used.

For example, there may be mentioned a mutation separation method which uses a mutagen (Kobo Bunshi Idengaku Jikken-ho (Methods for Yeast Molecular Genetics Experimentation), 1996, Gakkai Shuppan Center), a random mutation method which makes use of PCR (polymerase chain reaction) (PCR Methods Appl., 1992, vol. 2, p. 28-33) and the like.

In addition, the PDC gene in which a mutation was introduced into a part thereof may express a temperature-sensitive mutant type pyruvate decarboxylase. The temperature-sensitive mutant type pyruvate decarboxylase is an enzyme which shows an activity equivalent to that of the wild type pyruvate decarboxylase at a certain culture temperature but shows disappearance or lowering of the activity at a specific culture temperature or more.

A mutant which expresses such a mutant type pyruvate decarboxylase can be obtained by selecting a strain which shows a growth rate identical to that of the wild type yeast under such a temperature condition that the activity is not limited but the growth rate is considerably lowered under a specific temperature by which the activity is restricted.

<Host>

A mutant of *S. pombe* in which a PDC gene is deleted or inactivated can be used as a host for producing the transformant of the present invention. In addition, an *S. pombe* strain in which a specific gene other than PDC genes is further deleted or inactivated in addition to the PDC gene can also be used as the host. The *S. pombe* host in which a specific gene other than PDC genes is deleted or inactivated is described, for example, in International Publication No. 2002/101038, International Publication No. 2007/015470 and the like. By deleting or inactivating a protease gene or the like, expression efficiency of a heterogeneous protein can be improved, and, by applying it as a host of the present invention, improvement of lactic acid production efficiency can be expected.

In addition, as the *S. pombe* to be used as the host, it is preferable to use those which have a marker for selecting a transformant. For example, it is preferable to use a host for which a specific nutrient component is essential for growth due to deletion of a certain gene. By introducing this deleted gene (auxotrophic complementary marker) into a vector in advance, auxotrophic nature of the host disappears in the transformant. By the difference in the auxotrophic nature between the host and transformant, a transformant can be obtained by discriminating them.

For example, when an *S. pombe* strain which became uracil-less due to deletion or inactivation of orotidyl phosphate decarboxylase gene (ura 4 gene) is used as a host, transformation is carried out using a vector having the ura 4 gene (auxotrophic complementary marker) and then those from which the uracil-less was disappeared are selected, thereby, a transformant into which the vector was introduced can be obtained. The gene which causes auxotrophy due to its deletion in the host is not limited to the ura 4 gene as long as it can be used in the selection of transformants, and it may be an isopropyl malate dehydrogenase gene (leu 1 gene) and the like.

In addition, an *S. pombe* strain in which PDC genes are not deleted nor inactivated can also be used as a host for the production of a transformant. As the host in that case, those in which the aforementioned gene other than PDC genes (aux-otrophy marker, protease gene and the like) are deleted or inactivated can be used. The transformant can be produced using this host and then a part of PDC genes of the transformant are deleted or inactivated, so that, the transformant of the present invention can be obtained.

<Lactate Dehydrogenase Gene>

The transformant of the present invention has a lactate dehydrogenase gene (a gene encoding lactate dehydrogenase, to be referred also to as "LDH gene" hereinafter). As described in the foregoing, *S. pombe* does not have the LDH gene by nature. Accordingly, the transformant is obtained by introducing an LDH gene of an organism other than *S. pombe* into *S. pombe* by genetic engineering techniques.

The LDH gene concerned in the present invention is not particularly limited, and for example, there may be mentioned an LDH gene derived from the microorganisms belonging to the genus Bifidobacterium, the genus Lactobacillus and the like and an LDH gene derived from mammals such as human and the like. Particularly, a mammal-derived LDH gene is preferable from the viewpoint of superior efficiency of lactic acid production by *S. pombe*. Particularly, a human-derived LDH gene is more preferable (reference: Tsujibo H, Tiano H F, Li S S-L. Nucleotide sequence of the cDNA and an intronless pseudogene for human lactate dehydrogenase-A isozyme. Eur. J. Biochem., (1985) 147, 9-15). The LDH gene described in SEQ ID NO: 1 of the following SEQUENCE LISTING is further preferable.

<Production of Transformant>

The transformant of the present invention is obtained by using an *S. pombe* in which a part of PDC genes is deleted or inactivated as the host and introducing an LDH gene into this *S. pombe* by genetic engineering techniques. In addition, the transformant of the present invention can also be obtained by using an *S. pombe* in which PDC genes are not deleted nor inactivated as the host, obtaining a transformant by introducing an LDH gene into this *S. pombe* by genetic engineering techniques, and then deleting or inactivating a part of the PDC genes of the thus obtained transformant. In the Examples which are described later, the transformant of interest was produced by the former method, but almost equivalent transformant can also be produced by the latter method. In the following, the production method of transformant is described based on the former method.

As the method for introducing LDH gene into a host by genetic engineering techniques, a conventionally known method can be used. As the method for introducing structural gene of a heterogeneous protein into *S. pombe* as the host, the methods described in JP-A-5-15380, International Publication No. 95/09914, JP-A-10-234375, JPA-2000-262284, JP-A-2005-198612 and the like can for example be used.

It is preferred that LDH gene is introduced into a chromosome of *S. pombe*. By introducing the LDH gene into a chromosome, a transformant having an excellent maintaining stability in subculturing can be obtained. In addition, two or more of the LDH gene can also be introduced into a chromosome. By introducing two or more LDH genes, expression efficiency of the LDH gene can be increased, and it is considered therefore that the production efficiency of lactic acid is improved. According to the transformant of the present invention, the number of LDH genes introduced into a chromosome is preferably from 1 to 20, and particularly preferably from 1 to 8.

As the method for introducing LDH gene into a chromosome, a conventionally known method can be used. For example, two or more of LDH gene can be introduced into a chromosome by the method described in the aforementioned JP-A-2000-262284. Also, one LDH gene can also be introduced into a chromosome by this method. In addition, as will be described later, one or two or more of LDH gene can also be introduced into two or more sites of a chromosome.

As the method for introducing LDH gene into a chromosome of *S. pombe*, a method in which it is introduced by a homologous recombination method using a vector which has an expression cassette having LDH gene and a recombination site is preferred. The vector and homologous recombination method to be used in this method are described in the following.

<Vector>

The vector has an expression cassette having LDH gene and a recombination site.

The expression cassette is a combination of DNA necessary for expressing lactate dehydrogenase and contains LDH gene, a promoter which functions in *S. pombe* and a terminator which functions in *S. pombe*. In addition, it may contain at least one of the 5'-nontranslation region and 3'-nontranslation region. Further, it may contain the aforementioned auxotrophic complementary marker. Preferred expression cassette is an expression cassette which contains an LDH gene, a promoter, a terminator, a 5'-nontranslation region, a 3'-nontranslation region, and an auxotrophic complementary marker. Two or more LDH genes may be present in the expression cassette. The number of LDH genes in the expression cassette is preferably from 1 to 8, and more preferably from 1 to 5.

The promoter and terminator which function in *S. pombe* may be those which can maintain expression of lactate dehydrogenase by functioning in the transformant even when it becomes acidic (even when it becomes pH 6 or less) due to accumulation of lactic acid by the transformant of the present invention. As the promoter which functions in *S. pombe*, a promoter originally possessed by *S. pombe* (a substance having high transcription initiation activity is preferable), a promoter which is not originally possessed by *S. pombe* (a virus-derived promoter and the like), and the like can be used. In this connection, two or more promoters may be present in the vector.

As the promoter originally possessed by *S. pombe*, for example, there may be mentioned an alcohol dehydrogenase gene promoter, an nmt 1 gene promoter concerned in the metabolism of thiamin, a fructose-1,6-bisphosphatase gene promoter concerned in the metabolism of glucose, an invertase gene promoter concerned in catabolite inhibition (cf., International Publication No. 99/23223), a heat shock protein gene promoter (cf., International Publication No. 2007/26617) and the like.

As the promoter which is not originally possessed by *S. pombe*, for example, there may be mentioned the animal cell virus-derived promoters described in JP-A-5-15380, JP-A-7-163373 and JP-A-10-234375, of which hCMV promoter and SV40 promoter are preferable.

As the terminator which functions in *S. pombe*, a terminator originally possessed by *S. pombe* and a terminator which is not originally possessed by *S. pombe* can be used. In this connection, two or more terminators may be present in the vector.

As the terminator, for example, there may be mentioned the human-derived terminators described in JP-A-5-15380, JP-A-7-163373 and JP-A-10-234375, of which a human lipocortin I terminator is preferable.

The recombination region of the vector is a region having a base sequence which can carry out homologous recombination with the target region of the homologous recombination in the *S. pombe* chromosome. Also, the target region is a region which becomes a target for introducing the expression cassette into the *S. pombe* chromosome. The target region can be freely set by changing the recombination region of the vector to such a base sequence that it can carry out homologous recombination with the target region.

It is necessary that homology of the aforementioned base sequence of recombination region with the base sequence of target region is 70% or more. Also, from the viewpoint of causing homologous recombination easily, homology of the base sequence of recombination region with the base sequence of target region is preferably 90% or more, and more preferably 95% or more. By the use of a vector having such a recombination region, the expression cassette is introduced into the target region by homologous recombination.

It is preferable that the length of recombination region (the number of bases) is from 20 bp to 2000 bp. When the length of recombination region is 20 bp or more, homologous recombination easily occurs. Also, when the length of recombination region is 2000 bp or less, it becomes easy to prevent difficulty in occurring homologous recombination due to too long size of the vector. The length of recombination region is more preferably 100 bp or more, and further preferably 200 bp or more. Also, the length of recombination region is more preferably 800 bp or less, and further preferably 400 bp or less.

The vector may have another DNA region in addition to the aforementioned expression cassette and recombination region. For example, there may be mentioned a replication initiation region which is called "ori" and necessary for replication in *Escherichia coli* and antibiotics resistance genes (neomycin resistance gene and the like) and the like. These are genes which are generally required when a vector is constructed using *Escherichia coli*. However, it is preferable that the above-mentioned replication initiation region is removed when the vector is introduced into the chromosome of the host as described later.

The vector is a vector which has a cyclic DNA structure or linear DNA structure, and it is preferable to be introduced in a linear DNA structure when introduced into the cells of *S. pombe*. That is, in the case of a vector having a cyclic DNA structure such as a generally used plasmid DNA, it is preferable to be introduced it into the cells of *S. pombe* after cutting open the vector into linear form using a restriction enzyme.

In this case, the position where the vector having a cyclic DNA structure is cut open is within the recombination region. By this, the recombination region is partially present respectively in both termini of the cut open vector, so that the entire vector is introduced into target region of a chromosome by homologous recombination.

The vector may be constructed by a method other than the method for cutting open a vector having a cyclic DNA structure, with the proviso that it can make a linear DNA structure in which parts of the recombination region are present respectively in both termini thereof.

As the vector, for example, an *Escherichia coli*-derived plasmid such as pBR322, pBR325, pUC118, pUC119, pUC18, or pUC19 can be suitably used.

In this case, it is preferable that, at the time when the plasmid vector is used in homologous recombination, a replication initiation region which is called "ori" and necessary for replication in *Escherichia coli* is removed therefrom. By this, when the above-mentioned vector is introduced into a chromosome, its introduction efficiency can be improved.

The construction method of a vector from which the replication initiation region was removed is not particularly limited, but it is preferable to use the method described in JP-A-2000-262284. That is, preferred is a method in which a precursor vector wherein the replication initiation region is inserted into a cutting position of the recombination region is constructed in advance, so that a linear DNA structure can be obtained in the aforementioned manner and, at the same time, the replication initiation region is cutout. By this, a vector from which the replication initiation region was removed can be obtained conveniently.

In addition, it may be a method for obtaining a vector to be used in homologous recombination, in which a precursor vector having an expression cassette and a recombination region is constructed by applying the expression vectors and their construction methods described in JP-A-5-15380, JP-A-7-163373, International Publication No. 96/23890, JP-A-10-234375 and the like, and then the replication initiation origin is removed from the precursor vector by general genetic engineering techniques.

<Target Region>

The target region into which the vector is introduced may be present in only one position in *S. pombe* chromosome or may be present in two or more positions thereof. When the target region is present in two or more positions, the vector to be introduced into *S. pombe* chromosome can be arranged in two or more positions. Also, when the LDH gene in the expression cassette is set to two or more, two or more LDH genes can be introduced into one position of the target region. Further, the expression cassette can be introduced into two or more kinds of target regions using two or more kinds of vectors having recombination regions corresponding to the respective target regions. By these methods, two or more of the LDH gene can be introduced into *S. pombe* chromosome, and by this, expression level of lactate dehydrogenase can be increased and productivity of lactic acid can therefore be improved.

When the expression cassette is introduced into one target region, the method described for example in JP-A-2000-262284 can be used. Using two or more kinds of vectors having different recombination regions, respective vectors can be introduced into different target regions. However, this method is complicated when vectors are introduced into two or more positions of the chromosome.

When mutually and substantially identical base sequence moieties presenting in two or more positions in a chromosome can be used as target regions and vectors can be introduced into the respective two or more positions of target regions, vectors can be introduced into two or more positions of the chromosome using one kind of the vector. The mutually and substantially identical base sequences mean that homology of the base sequences is 90% or more. It is preferable that homology between the target regions is 95% or more. In addition, the length of mutually and substantially identical base sequences is a length which includes the recombination region of the aforementioned vector and is preferably 1000 bp or more. In comparison with the case in which two or more LDH genes are introduced into one target region, even when the number of introduced LDH genes is the same, it is rare that the LDH genes are dropped out of the chromosome at one time in growing the transformant when the LDH genes are introduced by dispersing into two or more target regions, so that maintaining stability of the transformant by sub-culturing is improved.

As the target region which is present in two or more positions in a chromosome, a transposon gene Tf2 is preferable. It is known that the Tf2 is a transposon gene which is present at a total of 13 positions respectively in 3 (haploid) chromosomes of *S. pombe*, its length (the number of basis) is about 4900 bp and the base sequence homology among these genes is 99.7% (cf., the following reference).

Nathan J. Bowen et al., "Retrotransposons and Their Recognition of pol II Promoters: A Comprehensive Survey of the Transposable Elements From the Complete Genome Sequence of *Schizosaccharomyces pombe* ", Genome Res., 2003, 13: 1984-1997

A vector can be introduced into only one position of T12 presenting in 13 positions of a chromosome. In this case, a transformant having two or more of the LDH gene can be obtained by introducing a vector having two or more of the LDH gene. Also, a transformant having two or more of the LDH gene can be obtained by introducing the vector into two or more positions of Tf2. In this case, a transformant having a further large number of the LDH gene can be obtained by introducing a vector having two or more of the LDH gene. When a vector is introduced into all of the 13 positions of Tf2, there is a possibility that load on the survival and growth of the transformant becomes too large. Preferably, it is preferable that a vector is introduced into 8 positions or less of the 13 positions of Tf2 and it is more preferable that a vector is introduced into 5 positions or less thereof.

<Transformation Method>

As the method for transforming an *S. pombe* host by a homologous recombination method, a conventionally known homologous recombination method can be used. Preferred as the transformation method of the present invention is a method in which the above-mentioned *S. pombe* wherein a part of PDC genes is deleted or inactivated is used as a host, and an expression cassette is introduced into its chromosome by homologous recombination using the above-mentioned vector. According to this production method, the transformant of the present invention can be produced conveniently.

According to the transformation method of the present invention, in general, after carrying out homologous transformation, transformants obtained are subjected to selection. As the selection method, for example, the method shown below can be mentioned. Screening is carried out by a medium which can select transformants by the aforementioned auxotrophic marker, and from the obtained colonies, two or more thereof are elected. Next, they are separately liquid-cultured, expression level of heterogeneous protein in each culture is examined and then transformants showing higher expression level of the heterogeneous protein are selected. In addition, by carrying out a genomic analysis of these selected transformants by pulse field gel electrophoresis, the number of vectors and the number of expression cassette introduced into a chromosome can be examined.

The number of vectors to be introduced into a chromosome can be adjusted to a certain degree by adjusting introduction conditions and the like, but it is considered that the introduction efficiency and the number of introductions also change depending on the size (the number of bases) and structure of the vector.

It is considered that expression level of lactate dehydrogenase can be increased and productivity of lactic acid can therefore be improved by introducing two or more of LDH gene into *S. pombe* chromosome. However, the object of the present invention is to obtain a transformant achieving high productivity of lactic acid and is not to obtain a transformant merely having further larger number of expression cassettes. In general, it is expected that expression efficiency of lactate dehydrogenase is increased and production efficiency of lactic acid is therefore increased, as the number of expression cassettes increases. However, it is also considered that when the number of expression cassettes is too large, load on the survival and growth of cells becomes large and production efficiency of lactic acid may be therefore lowered. In addition, it is considered that when size of the vector becomes large, probability of being introduced into a chromosome is lowered, it becomes difficult to increase the number of vectors to be introduced, and it therefore becomes difficult to obtain the transformant itself.

[Production Method of Lactic Acid]

The production method of lactic acid of the present invention is a method for producing lactic acid by culturing the transformant of the present invention in culture and obtaining lactic acid from the culture liquid.

By culturing the transformant of the present invention in a culture containing a sugar, pyruvic acid obtained from the sugar by the glycolytic pathway is reduced by lactate dehydrogenase to generate lactic acid, and the lactic acid generated into the culture is recovered from the culture, so that lactic acid can be produced.

Regarding the culture to be used in the production of lactic acid, a conventionally known yeast culture medium containing a sugar can be used, and it may further contain a nitrogen sources, inorganic salts and the like which can be assimilated by S. pombe and can carry out culturing of S. pombe efficiently. As the culture, a natural medium may be used or a synthetic medium may be used.

As a sugar as a carbon source, for example, there may be mentioned sugars such as glucose, fructose, sucrose, and maltose. As the nitrogen source, for example, there may be mentioned an ammonia, an ammonium salt of inorganic acid or inorganic acid such as ammonium chloride and ammonium acetate, peptone, casamino acid, yeast extract and the like. As the inorganic salts, for example, there may be mentioned magnesium phosphate, magnesium sulfate, sodium chloride and the like. In addition, a fermentation accelerator and the like such as proteolipid can be contained.

According to the lactic acid production method of the present invention, it is preferable to use a culture which contains especially glucose as the sugar. Glucose concentration of the culture (100% by mass) in the initial stage of culturing is preferably 1% by mass or more, more preferably from 1% by mass to 50% by mass, and further preferably from 2% by mass to 16% by mass. Since the glucose concentration is lowered by the culturing, it is preferable to continue the culturing by adding glucose in response to the necessity. Glucose concentration at the final stage of culturing may become 1% by mass or less. In addition, when the culturing is continuously carried out by circulating the culture while separating lactic acid, it is preferable to keep the above-mentioned glucose concentration. By setting the glucose concentration to 2% by mass or more, the productivity of lactic acid is further improved. Also, by setting glucose in the culture to 16% by mass or less, the production efficiency of lactic acid is further improved.

In addition, for the purpose of increasing productivity of lactic acid production, it is preferable to carry out a high density culturing. In the high density culturing, it is preferable that initial cell density of the transformant in the culture is set to from 0.1 g/L to 50 g/L, on the dry cell weight basis. It is more preferable that initial cell density of the transformant in the culture is set to from 0.2 g/L to 40 g/L, on the dry cell weight basis. By increasing the initial cell density, a high productivity can be attained within short period of time. In addition, when the initial cell density is too high, there is a possibility of causing a problem such as aggregation of cells or lowering of purification efficiency.

In this connection, the cell density shown in the examples and the like which are described later is a value converted from the absorbance of light having a wavelength of 660 nm (OD660) measured by a visible-ultraviolet spectrometer V550 manufactured by JASCO Corporation. The OD=1 at 660 nm corresponds to 0.2 g dry weight and 0.8 g wet weight, of the fission yeast.

In the culturing, a conventionally known yeast culturing method can be used, and for example, it can be carried out by a shaking culture, an agitation culture and the like.

In addition, it is preferable that culturing temperature is from 23° C. to 37° C. Also, culturing time can be optionally determined.

In addition, the culturing may be a batch culture or may be a continuous culture. For example, after carrying out the culturing by a batch culture, a culture containing lactic acid can be obtained by separating cells from the culture. Also, in the case of a continuous culture method, for example, there may be mentioned a method in which culturing is continuously carried out by repeating the steps of drawing out a part of the culture from the culture vessel in the course of culturing, separating lactic acid from the drawn out culture while recovering the culture supernatant, and returning the culture supernatant to the culture vessel after adding glucose and fresh culture thereto. By carrying out continuous culture, productivity of lactic acid is further improved.

According to the lactic acid production method which uses the transformant of the present invention, even when pH becomes low (approximately a pH of from 2 to 4) due to the accumulation of lactic acid, lactic acid can be produced without carrying out neutralization. Thus, even after pH of the culture becomes 4 or less, lactic acid can be produced by continuous culture which further continues the culturing. The pH at the final stage of culturing or the pH during continuous culture is preferably from 1 to 4, particularly preferably from 1.5 to 3.5. For the purpose of increasing productivity of lactic acid, it is preferable to further continue the culturing when pH of the culture became 3.5 or less. Since the transformant of the present invention is excellent in acid resistance, its culturing can be continued without neutralizing the lactic acid in the culture produced by the transformant.

A conventionally known method can be used in obtaining lactic acid from the culture. Particularly, it is preferable to obtain lactic acid by separating the culture and lactic acid without neutralizing the lactic acid in the culture. For example, there may be mentioned a method in which, after separating cells from the culture after completion of the culturing by centrifugation and adjusting the pH to 1 or less, extraction is carried out with diethyl ether, ethyl acetate and the like, a method in which, after adsorption to an ion exchange resin and subsequent washing, elution is carried out, a method in which impurities are removed using activated carbon, a method in which distillation is carried out after allowing to react with an alcohol in the presence of an acid catalyst, and a method in which separation is carried out using a separation membrane. In addition, in some cases, lactic acid can be obtained by neutralizing the lactic acid in the culture and then separating the culture and the lactic acid salt. For example, lactic acid can also be obtained by a method in which the lactic acid in the culture is converted into calcium salt or lithium salt and this neutralized salt is crystallized.

Since the lactic acid production method of the present invention described in the above uses, as a host, a transformant prepared from S. pombe which is particularly excellent in acid resistance, lactic acid can be produced conveniently with a high productivity without carrying out neutralization with an alkali. In addition, since the efficiency of ethanol fermentation is lowered due to deletion or inactivation of a part of the PDC genes, the sugar base yield of lactic acid (ratio of produced amount of lactic acid based on the amount of consumed sugar) is improved. According to the present invention, the sugar base yield of lactic acid can be easily increased to 50% by mass or more. In some cases, sugar base yield of lactic acid reaches 70% by mass or more. In addition, the lactic acid production method of the present invention is also suited for the high density culturing in the presence of a high concentration of glucose and by a high concentration of the transformant.

EXAMPLES

The following describes the present invention in detail by showing examples and comparative examples. However, the present invention is not restricted by the following descriptions. In this connection, the term "%" as used in these examples means "% by mass" unless otherwise noted.

Example 1

<Preparation of S. pombe Gene Deletion Strain>

A uracil-less strain of S. pombe (ARC 010, genotype: h-leu1-32 ura4-D18, received from Professor Yuichi Iino at The University of Tokyo, Graduate School of Science, Molecular Genetics Research Laboratory) was transformed in accordance with the Latour method (described in Nucleic Acids Res., 2006, vol. 34, p. e11, International Publication No. 2007/063919) to prepare a deletion strain from which a pyruvate decarboxylase (PDC) gene and an alcohol dehydrogenase (ADH) gene were deleted.

For the preparation of deletion fragments, a complete genomic DNA prepared using DNeasy (manufactured by QIAGEN) from an S. pombe strain ARC 032 (genotype: h-, received from Professor Yuichi Iino at The University of Tokyo, Graduate School of Science, Molecular Genetics Research Laboratory) was used as the template, and the 8 species of synthetic oligo-DNA (manufactured by Operon) having respective sequence shown in the following were used for each of the genes to be deleted.

(1) An origo-DNA for preparation of pdc1 (systemic name: SPAC13A11.06) deletion fragment.
UF: 5'-AGGCAAATCG TGAACTCGG-3' (SEQ ID NO: 2 of the following SEQUENCE LISTING)
UR: 5'-GCCAATTCCA CTCTCAATAG CCCGAACGTT CCGTCTCG-3' (SEQ ID NO: 3 of the following SEQUENCE LISTING)
OF: 5'-GCTATTGAGA GTGGAATTGG C-3' (SEQ ID NO: 4 of the following SEQUENCE LISTING)
OR: 5'-AGTGGGATTT GTAGCTAAGC TACTGGTTTC CACATTGTTT GG-3' (SEQ ID NO: 5 of the following SEQUENCE LISTING)
DF: 5'-AAGTTTCGTC AATATCACAA GCTCGAGACG GAACGTTCGG-3' (SEQ ID NO: 6 of the following SEQUENCE LISTING)
DR: 5'-TTACAATGCT GAGTGTGTAT TCC-3' (SEQ ID NO: 7 of the following SEQUENCE LISTING)
FF: 5'-TGAACTCGGT TGAAAAATGT CG-3' (SEQ ID NO: 8 of the following SEQUENCE LISTING)
FR: 5'-TGAGTGTGTA TTCCTTTTTC GC-3' (SEQ ID NO: 9 of the following SEQUENCE LISTING)

(2) An origo-DNA for preparation of pdc2 (systemic name: SPAC1F8.07c) deletion fragment.
UF: 5'-CTCTCCAGCT CCATCCATAA G-3' (SEQ ID NO: 10 of the following SEQUENCE LISTING)
UR: 5'-GACACAACTT CCTACCAAAA AGCCTTTCTG CCCATGTTTT CTGTC-3' (SEQ ID NO: 11 of the following SEQUENCE LISTING)
OF: 5'-GCTTTTTGGT AGGAAGTTGT GTC-3' (SEQ ID NO: 12 of the following SEQUENCE LISTING)
OR: 5'-AGTGGGATTT GTAGCTAAGC TGTATCCATT TCAGCCGTTT GTG-3' (SEQ ID NO: 13 of the following SEQUENCE LISTING)
DF: 5'-AAGTTTCGTC AATATCACAA GCTGACAGAA AACATGGGCA GAAAG-3' (SEQ ID NO: 14 of the following SEQUENCE LISTING)
DR: 5'-GTTCCTTAGA AAAAGCAACT TTGG-3' (SEQ ID NO: 15 of the following SEQUENCE LISTING)
FF: 5'-CATAAGCTTG CCACCACTTC-3' (SEQ ID NO: 16 of the following SEQUENCE LISTING)
FR: 5'-GAAAAAGCAA CTTTGGTATT CTGC-3' (SEQ ID NO: 17 of the following SEQUENCE LISTING)

(3) An origo-DNA for preparation of pdc3 (systemic name: SPAC186.09) deletion fragment.
UF: 5'-AAGGCATATT CGTTGATTAA CCC-3' (SEQ ID NO: 18 of the following SEQUENCE LISTING)
UR: 5'-GGTGGAAAGG TTTGTGCAAT CCGTCAACTC ATGATATTTC TTTATGG-3' (SEQ ID NO: 19 of the following SEQUENCE LISTING)
OF: 5'-GATTGCACAA ACCTTTCCAC C-3' (SEQ ID NO: 20 of the following SEQUENCE LISTING)
OR: 5'-AGTGGGATTT GTAGCTAAGC TCATCCCACA TCTGTAATAA TCACG-3' (SEQ ID NO: 21 of the following SEQUENCE LISTING)
DF: 5'-AAGTTTCGTC AATATCACAA GCTCCATAAA GAAATATCAT GAGTTGACG-3' (SEQ ID NO: 22 of the following SEQUENCE LISTING)
DR: 5'-TTTGAGAAGA AAATTTTATG TCCAGC-3' (SEQ ID NO: 23 of the following SEQUENCE LISTING)
FF: 5'-CCATTTAGCA GTATAAGGGT CG-3' (SEQ ID NO: 24 of the following SEQUENCE LISTING)
FR: 5'-AAGTAAAAAT GTGAAAGCAA TGTAGG-3' (SEQ ID NO: 25 of the following SEQUENCE LISTING)

(4) An origo-DNA for preparation of pdc4 (systemic name: SPAC3G9.11c) deletion fragment.
UF: 5'-ACACACAAAC ACTTCCATTC C-3' (SEQ ID NO: 26 of the following SEQUENCE LISTING)
UR: 5'-CCTAACAAAA GCATCATTTG AGAAGACGAA TGAAATGACA GCAAC-3' (SEQ ID NO: 27 of the following SEQUENCE LISTING)
OF: 5'-TTCTCAAATG ATGCTTTTGT TAGG-3' (SEQ ID NO: 28 of the following SEQUENCE LISTING)
OR: 5'-AGTGGGATTT GTAGCTAAGC TCTGGACAAG TCTACCTTGG AG-3' (SEQ ID NO: 29 of the following SEQUENCE LISTING)
DF: 5'-AAGTTTCGTC AATATCACAA GCTGTTGCTG TCATTTCATT CGTC-3' (SEQ ID NO: 30 of the following SEQUENCE LISTING)
DR: 5'-GATACAGGAG TACAACAAAA CAC-3' (SEQ ID NO: 31 of the following SEQUENCE LISTING)
FF: 5'-TCTCCATCCC TCCTCCC-3' (SEQ ID NO: 32 of the following SEQUENCE LISTING)
FR: 5'-ACGCTACTTA AACAAGACAA GC-3' (SEQ ID NO: 33 of the following SEQUENCE LISTING)

(5) An origo-DNA for preparation of adh1 (systemic name: SPCC13B11.01) deletion fragment.
UF: 5'-TCATTCCTCG ATATTCAGTT C-3' (SEQ ID NO: 34 of the following SEQUENCE LISTING)
UR: 5'-GCCAGTGGGA TTTGTAGCTA CTCTGATCGG CATTTTTTGG-3' (SEQ ID NO: 35 of the following SEQUENCE LISTING)
OF: 5'-GTTTCGTCAA TATCACAAGC TTCCCCAACC TCCCATTTCC TCC-3' (SEQ ID NO: 36 of the following SEQUENCE LISTING)
OR: 5'-CTACGATCAG AAGAAGATCA ATGAGACGCG GAAGGGGAGC GCC-3' (SEQ ID NO: 37 of the following SEQUENCE LISTING)

DF: 5'-GGCGCTCCCC TTCCGCGTCT CATTGATCTT CTTCTGATCG TAG-3' (SEQ ID NO: 38 of the following SEQUENCE LISTING)
DR: 5'-ATGCATTTCA CTCTATTCCT C-3' (SEQ ID NO: 39 of the following SEQUENCE LISTING)
FF: 5'-GCTATAGTTA AGTGTAAGAC-3' (SEQ ID NO: 40 of the following SEQUENCE LISTING)
FR: 5'-TTGTCCACAC CACTCATTCG-3' (SEQ ID NO: 41 of the following SEQUENCE LISTING)
(6) An origo-DNA for preparation of adh4 (systemic name: SPAC5H10.06c) deletion fragment.
UF: 5'-ATCGTCGTCG ATGCTGATTG G-3' (SEQ ID NO: 42 of the following SEQUENCE LISTING)
UR: 5'-GCCAGTGGGA TTTGTAGCTC AGCAGT-CATT CTCATTCCG-3' (SEQ ID NO: 43 of the following SEQUENCE LISTING)
OF: 5'-CGTCAATATC ACAAGCTTGT CTCCCCTTCT ATTGGGATTT GC-3' (SEQ ID NO: 44 of the following SEQUENCE LISTING)
OR: 5'-GATTACCTGC AATCATGTTT CCGGCCTTTT GTGAAACCTG CC-3' (SEQ ID NO: 45 of the following SEQUENCE LISTING)
DF: 5'-GGCAGGTTTC ACAAAAGGCC GGAAA-CATGA TTGCAGGTAA TC-3' (SEQ ID NO: 46 of the following SEQUENCE LISTING)
DR: 5'-GGAGAATGAT GTATTGGTAA ATAAC-3' (SEQ ID NO: 47 of the following SEQUENCE LISTING)
FF: 5'-CCTTGGGAAT GAGCGAATTC-3' (SEQ ID NO: 48 of the following SEQUENCE LISTING)
FR: 5'-GGGTTGTGAA GAGCATACTG-3' (SEQ ID NO: 49 of the following SEQUENCE LISTING)
(7) An origo-DNA for preparation of adhX (systemic name: SPBC1773.06c) deletion fragment
UF: 5'-GAAGGAGATT ATGTGAAACA AGT-TGAAATC-3' (SEQ ID NO: 50 of the following SEQUENCE LISTING)
UR: 5'-AGCTTAGCTA CAAATCCCAC TCT-GAGGGTA GTGTTCTTGC TACAAAAATC T-3' (SEQ ID NO: 51 of the following SEQUENCE LISTING)
OF: 5'-AAGTTTCGTC AATATCACAA GCTCATGACG GAAGATTCCG AGAAATTCCG TTT-3' (SEQ ID NO: 52 of the following SEQUENCE LISTING)
OR: 5'-CAAAGCCATG CTTTTAATGT TAAAGT-GAAT-3' (SEQ ID NO: 53 of the following SEQUENCE LISTING)
DF: 5'-ATTCACTTTA ACATTAAAAG CATGGCTTTG ATCGATTGAG ATTTTTGTAG CAAGAACACT-3' (SEQ ID NO: 54 of the following SEQUENCE LISTING)
DR: 5'-GGAAATGGTT CATGTGGACT GGGTTT-TATT-3' (SEQ ID NO: 55 of the following SEQUENCE LISTING)
FF: 5'-CCTGCTCTTA AAATGACGAA TGGT-GTAGGC-3' (SEQ ID NO: 56 of the following SEQUENCE LISTING)
FR: 5'-ATATAGTGCG ATATGGATGA AGGAGAA-GAG-3' (SEQ ID NO: 57 of the following SEQUENCE LISTING)
(8) An origo-DNA for preparation of akrY (systemic name: SPAC977.14c) deletion fragment
UF: 5'-ATCATAACTT ACTATATCGT GAAGAAGAGA-3' (SEQ ID NO: 58 of the following SEQUENCE LISTING)
UR: 5'-AGCTTAGCTA CAAATCCCAC TTAGAATGAG TAATTCAACT TCTTAAACCA C-3' (SEQ ID NO: 59 of the following SEQUENCE LISTING)
OF: 5'-AAGTTTCGTC AATATCACAA GCTTAGCTT AAAAGTAATA AGCTTCTATG TGA-3' (SEQ ID NO: 60 of the following SEQUENCE LISTING)
OR: 5'-TGAAGACATT TTATAAAACT TAAATAAAAA-3' (SEQ ID NO: 61 of the following SEQUENCE LISTING)
DF: 5'-TTTTTATTTA AGTTTTATAA AATGTCTTCA GAAATTTAAA TCTGTGGTTT AAGAAGTTGA-3' (SEQ ID NO: 62 of the following SEQUENCE LISTING)
DR: 5'-ACTTTGTTTA TTGTAGAAAG TCGAGCT-TGA-3' (SEQ ID NO: 63 of the following SEQUENCE LISTING)
FF: 5'-CAAAAGACAG GGGTCGGATT GATTCCT-TGG-3' (SEQ ID NO: 64 of the following SEQUENCE LISTING)
FR: 5'-TGTGCTGTTT TTCAAGTGGT CATGCGTTAC-3' (SEQ ID NO: 65 of the following SEQUENCE LISTING)

For each gene to be deleted, a UP region by UF and UR, an OL region by OF and OR and a DN region by DF and DR were respectively prepared by a PCR method which used KOD-Dash (manufactured by Toyobo C., Ltd.), and then, using these as respective templates, complete length deletion fragments were prepared by a similar PCR method which respectively used FF and FR. At the time of preparing the complete length deletion fragments, the following two species of synthetic oligo-DNA (manufactured by Operon) were used, the complete genomic DNA similarly prepared from the strain ARC 032 was used as a template, and a ura4 region fragment prepared by a similar PCR method was also used as a template.

5'-AGCTTAGCTA CAAATCCCAC T-3' (SEQ ID NO: 66 of the following SEQUENCE LISTING)
5'-AGCTTGTGAT ATTGACGAAA CTT-3' (SEQ ID NO: 67 of the following SEQUENCE LISTING)

Strain names and deleted genes of the deletion strains prepared using respective deletion fragments prepared are shown in Table 1.

TABLE 1

| Strain names of gene deletion strains | Deleted genes Parenthesized are systemic names of genes |
|---|---|
| IGF 541 | pdc 4 (SPAC3G9.11c) |
| IGF 542 | pdc 1 (SPAC13A11.06) |
| IGF 543 | pdc 2 (SPAC1F8.07c) |
| IGF 544 | pdc 3 (SPAC186.09) |
| IGF 535 | adh1 (SPCC13B11.01) |
| IGF 545 | adh4 (SPAC5H10.06c) |
| IGF 550 | adhX (SPBC1773.06c) |
| IGF 546 | akrY (SPAC977.14c) |

Example 2

<Preparation of *S. pombe* Lactate Dehydrogenase Producer Strains>

Each of an uracil-less strain of *S. pombe* (ARC 010) and gene deletion strains of *S. pombe* prepared in Example 1 was transformed with a restriction enzyme BsiWI digest of a single position introduction type recombinant vector pXLT-HsLDH having a lactate dehydrogenase gene expression cassette, in accordance with the method of Bahler et al. (Yeast, 1998, vol. 14, pp. 943-951).

The pXLT-HsLDH was prepared by the process shown below. That is, firstly, an introduction type vector pXL4 for fission yeast use (Idiris et al., Yeast, 2006, vol. 23, pp. 83-99) was double-digested with restriction enzymes and the obtained fragment was subjected to blunt-end treatment and subsequently ligation. The thus obtained expression vector for fission yeast use, pXL1 (delta-neo) was further double-digested with restriction enzymes and the obtained fragment was subjected to blunt-end treatment and subsequently insertion by a top2 gene fragment cloned from the strain ARC 010 genome, thereby preparing a pXLT (5,558 base pairs) with its sequence (5'→3', cyclic) shown by SEQ ID NO:68 of SEQUENCE LISTING.

Next, a gene fragment encoding the human L-lactate dehydrogenase structural gene (HsLDH-ORF) described in a reference (Tsujibo et al., Eur. J. Biochem., 1985, vol. 147, pp. 9-15) was amplified by PCR using a human fibroblast cDNA library introduced into Okayama vector (reference: Okayama, H. and Berg, P.: A cDNA cloning vector that permits expression of cDNA inserts in mammalian cells. Mol. Cell. Biol., 3 (1983), 280-289) as a template and using the following primer set:

5'-GTCCATGGCA ACTCTAAAGG ATCAG-3' (No. 4620) (SEQ ID NO: 69 of the following SEQUENCE LISTING); and 5'-CAGTCGACTT AAAATTGCAG CTCCTTTTG-3' (No. 4621) (SEQ ID NO: 70 of the following SEQUENCE LISTING), in which a restriction enzyme NcoI recognition sequence is added to the 5'-terminal side, and a restriction enzyme SalI recognition sequence to the 3'-terminal side. The thus obtained amplification fragment was double-digested using restriction enzymes NcoI and SalI and then introduced into AflIII-SalI site of the multi-cloning vector pTL2M5 described in JP-A-2000-262284, thereby preparing an LDH expression vector pTL2HsLDH. Further, the expression cassette was cut out from the pTL2HsLDH by double digestion using restriction enzyme SpeI and Bst1107I and introduced into pXLT to prepare pXLT-HsLDH.

<Culture Test>

Each of the thus obtained transformants was inoculated into YPD 12 liquid medium (yeast extract 1%, peptone 2%, and glucose 12%) and cultured for 4.5 hours under conditions of 32° C. in temperature and 100 rpm in shaking rate. Lactic acid concentration in the culture at this time was measured using Bio Flow (Oji Scientific Instruments). A total of 20 hours of the culturing was further continued under the same conditions. Lactic acid concentration in the culture after 20 hours of the culturing was measured in the same manner.

Transformant strain names, host strain names, lactic acid concentration after 4.5 hours of culturing and lactic acid concentration after 20 hours of culturing are shown in Table 2.

TABLE 2

| Transformant strain name | Host strain name | Lactic acid conc. after 4.5 hours (g/L) | Lactic acid conc. after 20 hours (g/L) |
|---|---|---|---|
| ASP2832 | ARC010 | 9.9 | 16.3 |
| ASP2837 | IGF541 | 8.1 | 13.7 |
| ASP2838 | IGF542 | 46.1 | 88.1 |
| ASP2839 | IGF543 | 52.2 | 9.7 |
| ASP2840 | IGF544 | 8.2 | 13.8 |
| ASP2833 | IGF535 | 63.1 | 15.0 |
| ASP2834 | IGF545 | 8.7 | 14.2 |
| ASP2835 | IGF550 | 10.1 | 15.2 |
| ASP2836 | IGF546 | 0.0 | 10.0 |

Example 3

<Preparation of S. pombe Lactate Dehydrogenase High Producer Strain>

Since the strain IGF543 (h-leu1-32 ura4-D18 pdc2-D23) prepared in Example 1 was slow in its growth rate, in order to recover the growth rate, the strain IGF543 was streaked on YES plate (yeast extract 0.5%/glucose 3%/SP supplement) and cultured at 25° C., the thus obtained colonies were sub-cultured in YPD medium (yeast extract 1%/peptone 2%/glucose 2%) and cultured at 25° C., and using a sufficiently growing culture, a glycerol stock was prepared and preserved at −80° C. By repeating the above-mentioned procedure until an appropriate growth rate was obtained, a strain showing recovered growth rate was prepared (the name IGF543 was succeeded).

The pTL2HsLDH (Example 2) was double-digested with restriction enzyme SpeI and Bst1107I and the thus obtained fragment (hCMV promoter/LDH-ORF/LPI terminator) was inserted between restriction enzymes NheI-KpnI (smooth-ended) recognition sequences site of the Tf2 multi-position introduction type vector pTf2MCS-ura4 prepared by the following process, thereby preparing an introduction type L-lactate dehydrogenase gene expression vector pTL2HsLDH-Tf2.

Preparation process of the pTf2MCS-ura4 is as follows. That is, total genomic DNA of S. pombe was purified from cells using a total genomic DNA extraction kit (DNeasy, manufactured by QIAGEN), and using a 1 μg portion thereof as a template and using the following primer pairs in which a restriction enzyme BsiWI recognition sequence (CGTACG) was introduced into the 5' terminal side:

5'-AAGGCCTCGT ACGTGAAAGC AAGAGCAAAA CGA-3' (SEQ ID NO: 71 of the following SEQUENCE LISTING); and 5'-AAGGCCTCGT ACGTGCTTTG TCCGCTTGTA GC-3' (SEQ ID NO: 72 of the following SEQUENCE LISTING), a DNA fragment (about 3950 base pairs) of S. pombe Tf2-2 (systemic name: SPAC167.08 gene described in GeneDB) was amplified by the PCR method. By treating both termini of the amplified DNA fragment with a restriction enzyme BsiWI, this was separated and purified by an agarose gel electrophoresis and prepared as an insert fragment.

Next, a vector pXL4 for a chromosome introduction use (Idiris et al.,Yeast, vol. 23, pp. 83-99, 2006) was digested with the same restriction enzyme BsiWI to obtain a region (about 2130 base pair) containing an ampicillin resistance gene (ApR) and Escherichia coli replication origin (pBR322 ori). The DNA fragment was further subjected to a dephosphorylation treatment with a dephosphorylase (CIAP, manufactured by Takara Bio Inc.), separated and purified by an agarose gel electrophoresis and prepared as a vector fragment.

The above-mentioned insert fragment and vector fragment were ligated using a ligation kit (DNA Ligation Kit ver. 2, manufactured by Takara Bio Inc.) and then Escherichia coli DH5 (manufactured by Toyobo Co., Ltd.) was transformed to prepare a recombinant plasmid pTf2-2 (6071 base pairs).

Using 0.1 μg of the above-mentioned constructed vector pTf2-2 as a template and using the following primer pairs:

5'-GGGGTACCAA GCTTCTAGAG TCGACTCCGG TGCTACGACA CTTT-3' (having recognition sequences of restriction enzymes KpnI, HindIII, XbaI and SalI in the 5'-terminus) (SEQ ID NO: 73 of the following SEQUENCE LISTING); and 5'-GGGGTACCAG GCCTCTCGAG GCTAGCCATT TCCAGCGTAC ATCCT-3' (having recognition sequences of restriction enzymes KpnI, StuI, XhoI and NheI in the 5'-terminus) (SEQ ID NO: 74 of the following SEQUENCE LISTING), its full length was amplified by the PCR method to obtain a fragment of 6060 base pairs. Both termini thereof were digested with KpnI, a separation and purification with an agarose gel electrophoresis was conducted, and then, autocyclization using a ligation kit was carried out to thereby prepare a vector pTf2(MCS) of 6058 base pairs having a multi-cloning site (MCS) further inside of a transposon gene Tf2-2 sequence.

The above-mentioned constructed vector pTf2(MCS) was double-digested using restriction enzymes KpnI and NheI, and a fragment of 6040 base pairs was separated and purified by an agarose gel electrophoresis. Further, a fragment in which recognition sequences of restriction enzymes KpnI and NheI were added to both termini of a uracil-less marker ura4 of *S. pombe* (systemic name: SPCC330.05c described in GeneDB, orotidine-5'-phosphate decarboxylase gene) by PCR method was prepared and it was double-digested using restriction enzymes KpnI and NheI and then a fragment of 2206 base pairs was separated and purified by an agarose gel electrophoresis. These two fragments were ligated using the ligation kit to prepare a vector pTf2(MCS)-ura4 of 8246 base pairs having a multi-cloning site (MCS) further inside of the transposon gene Tf2-2 sequence.

Using the vector prepared in the above, the strain IGF543 (growth rate-recovered strain) was transformed by the method of Okazaki et al. (Okazaki et al., Nucleic Acids Res., 1990, vol. 18, pp. 6485-6489) and spread on a selection medium MMA+Leu plate. Each of a large number of the thus obtained single colonies was inoculated into a YPD 16 (yeast extract 1%/peptone 2%/glucose 16%) medium and cultured at 32° C. for 72 hours, and then, using the culture supernatant alone as a sample, measurement of concentrations of glucose, ethanol and L-lactic acid and medium pH was carried out using BF-4 and BF-5 (Oji Scientific Instruments). Based on the results, those having high lactic acid productivity were again selected, and again cultured using a YPD 12 (yeast extract 1%/peptone 2%/glucose 12%) medium (20 hours, 44 hours, 66.5 hours, 80 hours, 176 hours), and then concentrations of glucose, ethanol and L-lactic acid in the culture supernatant and medium pH were measured in the same manner and a strain having the highest productivity of L-lactic acid was selected and named ASP2782 (genotype: h⁻ leu1-32 ura4-D18 pdc2-D23 Tf2<HsLDH-ORF/ura4+).

A transformant of strain ARC010 was also prepared by the same process and named strain ASP2767.

Example 4 (Reference Example)

<Periodical Culturing Test using *S. pombe* Lactate Dehydrogenase High Producer Strain>

The transformant strain ASP2767 obtained in Example 3 was inoculated into a YPD 6 liquid medium (yeast extract 1%, peptone 2%, glucose 6%) and cultured for 24 hours under conditions of 32° C. in temperature and 100 rpm in shaking rate. After completion of the culturing, cells were recovered by centrifugation (2000 g, 10 minutes). Subsequently, the above-mentioned recovered cells were inoculated into 5 ml of a YPD 12 L liquid medium (yeast extract 1%, peptone 2%, glucose 12%, proteolipid 1%) to a density of 5.2 g (on the dry cell basis)/L (OD660 is 26) and cultured for 24 hours under conditions of 32° C. in temperature and 100 rpm in shaking rate, and concentrations of ethanol and lactic acid and pH in the culture were periodically measured. The results are shown in Table 3.

When the lactate dehydrogenase gene-introduced *S. pombe* was used, during a period of from 4 hours to 7 hours where pH of the culture becomes 2.9 or less due to accumulation of lactic acid, the pH was further lowered from 2.8 to 2.5 and concentration of lactic acid was increased, so that the lactic acid production was possible even under an acidic condition of pH 3 or less without carrying out neutralization with an alkali.

TABLE 3

| Culturing time (hr) | Ethanol conc. (g/L) | Lactic acid conc. (g/L) | pH |
|---|---|---|---|
| 1 | 4.0 | 2.9 | 3.7 |
| 2 | 7.8 | 6.7 | 3.2 |
| 4 | 16.0 | 21.5 | 2.8 |
| 7 | 28.0 | 44.7 | 2.5 |
| 24 | 28.5 | 37.7 | 2.5 |

Example 5 (Reference Example)

<High Density Culture Test using *S. pombe* Lactate Dehydrogenase High Producer Strain>

The transformant ASP2767 obtained in Example 3 was inoculated into the YPD 6 liquid medium (yeast extract 1%, peptone 2%, glucose 6%) and cultured for 24 hours under conditions of 32° C. in temperature and 100 rpm in shaking rate. After completion of the culturing, cells were recovered by centrifugation (2000 g, 10 minutes). Subsequently, the above-mentioned cells were inoculated into 5 ml of the YPD 12 L liquid medium (yeast extract 1%, peptone 2%, glucose 12%, proteolipid 1%) to a density of 0.4 g (on the dry cell basis)/L, 5.2 g/L, 18.2 g/L, 31.8 g/L or 48.0 g/L (OD660 is 2, 26, 91, 159 or 240, respectively) and respectively cultured under conditions of 32° C. in temperature and 100 rpm in shaking rate, and after the completion, concentrations of glucose, ethanol and lactic acid in the culture were measured. The results and the sugar base yield and production rate of lactic acid calculated from the measured results are shown in Table 4.

TABLE 4

| Initial cell density (g/L) | Culturing time (hr) | Glucose conc. (g/L) | Ethanol conc. (g/L) | Lactic acid conc. (g/L) | Sugar base yield of lactic acid (%) | Production rate of lactic acid (g/L/hr) |
|---|---|---|---|---|---|---|
| 0.4 | 24 | 0.0 | 26.7 | 34.1 | 26.5 | 1.4 |
| 5.2 | 7 | 0.4 | 28.0 | 44.7 | 34.8 | 6.4 |
| 18.2 | 4 | 0.8 | 24.1 | 61.1 | 47.7 | 15.3 |
| 31.8 | 2 | 28.7 | 18.8 | 48.0 | 47.9 | 24.0 |
| 48.0 | 2 | 6.8 | 21.9 | 62.7 | 51.3 | 31.3 |

Example 6

<High Density Culture Test using *S. pombe* Lactate Dehydrogenase High Producer Strain (pdc2 Deletion Strain)>

The transformant strain ASP2782 obtained in Example 3 was inoculated into the YPD 6 liquid medium (yeast extract 1%, peptone 2%, glucose 6%) and cultured for 24 hours under conditions of 32° C. in temperature and 100 rpm in shaking rate. After completion of the culturing, cells were recovered by centrifugation (2000 g, 10 minutes). Subsequently, the above-mentioned cells were inoculated into 5 ml of the YPD 12 L fermentation medium (yeast extract 1%, peptone 2%, glucose 12%, proteolipid 1%) to a density of 0.2 g (on the dry cell basis)/L, 3.8 g/L, 15.0 g/L, 23.8 g/L, 31.6 g/L or 46.8 g/L (OD660 is 1, 19, 75, 119, 158 or 234, respectively) and respectively cultured under conditions of 32° C. in temperature and 100 rpm in shaking rate, and after the completion, concentrations of glucose, ethanol and lactic acid in the culture were measured. The results and the sugar base yield and production rate of lactic acid calculated from the measured results are shown in Table 5.

TABLE 5

| Initial cell density (g/L) | Culturing time (hr) | Glucose conc. (g/L) | Ethanol conc. (g/L) | Lactic acid conc. (g/L) | Sugar base yield of lactic acid (%) | Production rate of lactic acid (g/L/hr) |
|---|---|---|---|---|---|---|
| 0.2 | 23 | 15.1 | 22.1 | 39.9 | 37.4 | 1.7 |
| 3.8 | 23 | 0.2 | 20.7 | 58.1 | 47.8 | 2.5 |
| 15.0 | 7 | 36.7 | 9.2 | 62.4 | 70.3 | 8.9 |
| 23.8 | 6 | 17.2 | 10.2 | 79.7 | 73.6 | 13.3 |
| 31.6 | 6 | 12.1 | 11.5 | 87.5 | 79.7 | 14.6 |
| 46.8 | 6 | 5.7 | 10.4 | 95.2 | 82.0 | 15.9 |

By the use of the strain ASP2782 in which the PDC2 was deleted, it was able to produce lactic acid with a high sugar base yield. In addition, as is shown by the cases in which the initial cell density was 15.0 g (on the dry cell basis)/L or more, it was found that the sugar base yield is sharply increased by carrying out the high density culturing. From this increase of sugar base yield, it was found that the transformant prepared by introducing lactate dehydrogenase gene into PDC2-deleted *S. pombe* has a highly optimized high expression system.

As shown in the aforementioned Table 4, in the case of Example 5 which used the transformant ASP2767 in which PDC2 was not deleted, the sugar base yield was low in comparison with this Example 6, and even the highest yield was merely about 50%. It is considered that this was because ethanol fermentation was carried out simultaneously with lactic acid fermentation due to no deletion of PDC2.

Example 7

<High Density Repeatedly Culture Test using *S. pombe* Lactate Dehydrogenase High Producer Strain (pdc2 Deletion Strain)>

The transformant ASP2782 obtained in Example 3 was inoculated into the YPD 6 liquid medium (yeast extract 1%, peptone 2%, glucose 6%) and cultured for 24 hours under conditions of 32° C. in temperature and 100 rpm in shaking rate. After completion of the culturing, cells were recovered by centrifugation (2000 g, 10 minutes). Subsequently, the above-mentioned cells were inoculated into 5 ml of the YPD 12 L liquid medium (yeast extract 1%, peptone 2%, glucose 12%, proteolipid 1%) to a density of about 30 g (on the dry cell basis)/L and cultured under conditions of 32° C. in temperature and 100 rpm in shaking rate, and concentrations of lactic acid and ethanol in the culture were measured. After completion of the culturing, culture supernatant and cells were recovered by centrifugation (2000 g, 10 minutes). The recovered cells were again added to the same liquid medium and their culturing was carried out. A series of these operations was further carried out 6 times. Each inoculation density and culturing time, measured results of concentrations of glucose, ethanol and lactic acid at the time of completion of the culturing, and sugar base yield of lactic acid calculated from the measured results, by a total of 7 times of the culturing, are shown in Table 6.

In the continuous culturing which used strain ASP2782, sugar base yield of lactic acid was maintained at high level even when the culturing was repeated, so that it was confirmed that lactic acid can be formed stably with high productivity without carrying out neutralization by a alkali.

TABLE 6

| | Initial cell density (g/L) | Culturing time (hr) | Glucose conc. (g/L) | Ethanol conc. (g/L) | Lactic acid conc. (g/L) | Sugar base yield of lactic acid (%) |
|---|---|---|---|---|---|---|
| 1st time | 38.6 | 23 | 0.7 | 11.5 | 97.2 | 81.2 |
| 2nd time | 35.8 | 6 | 0.0 | 18.1 | 93.1 | 72.4 |
| 3rd time | 29.2 | 42 | 0.0 | 14.5 | 86.5 | 75.2 |
| 4th time | 31.2 | 72 | 0.0 | 21.4 | 86.1 | 67.3 |
| 5th time | 28.6 | 24 | 0.0 | 19.3 | 84.6 | 69.1 |
| 6th time | 30.4 | 24 | 0.0 | 19.3 | 83.7 | 68.8 |
| 7th time | 30.6 | 24 | 4.1 | 19.3 | 83.3 | 68.8 |

Example 8

<Minimization of Medium>

The transformant strain ASP2782 obtained in Example 3 was inoculated into the YPD 6 liquid medium (yeast extract 1%, peptone 2%, glucose 6%) and cultured for 24 hours under conditions of 32° C. in temperature and 100 rpm in shaking rate. After completion of the culturing, cells were recovered by centrifugation (2000 g, 10 minutes). Subsequently, the above-mentioned cells were inoculated into 5 ml of the YPD 12 L liquid medium (yeast extract 1%, peptone 2%, glucose 12%, proteolipid 1%) or a D12 liquid medium (glucose 12%) to a density of 44.0 g (on the dry cell basis)/L and cultured under conditions of 32° C. in temperature and 100 rpm in shaking rate, and concentrations of lactic acid and ethanol were periodically measured. Culturing time, glucose concentration, ethanol concentration and lactic acid concentration in the culture and sugar base yield of lactic acid calculated from the measured results, on the two media, are shown in Table 7.

TABLE 7

| Medium | Culturing time (hr) | Glucose conc. (g/L) | Ethanol conc. (g/L) | Lactic acid conc. (g/L) | Sugar base yield of lactic acid (%) |
|---|---|---|---|---|---|
| YPD 12L | 6.0 | 0.4 | 13.7 | 96.3 | 78.2 |
| YPD 12L | 22.0 | 0.0 | 17.5 | 81.0 | 70.3 |
| D12 | 3.0 | 50.9 | 5.5 | 53.1 | 83.2 |
| D12 | 4.5 | 30.4 | 7.5 | 71.2 | 82.9 |
| D12 | 6.0 | 17.0 | 9.2 | 85.7 | 82.6 |

Example 9

<Results of Lactic Acid Production using *S. pombe* Lactate Dehydrogenase High Producer Strain>

Strain ASP2767 was inoculated into 5 ml of the YPD 24 L liquid medium (yeast extract 1%, peptone 2%, glucose 24%, proteolipid 1%) to a cell density of 0.2 g (on the dry cell basis)/L and cultured at 32° C. for 47 hours. Lactic acid production after completion of the culturing was 124.2 g/L. Strain ASP2767 was inoculated into 5 ml of the YPD 12LA liquid medium (yeast extract 1%, peptone 2%, glucose 12%, proteolipid 1%, CSL-AST 1%) to a cell density of 74.6 g (on the dry cell basis)/L and fermentation was carried out at 32° C. for 1 hour. Lactic acid production after completion of the fermentation was 58.6 g/L, and the production rate was 58.6 g/h.

Strain ASP2782 was inoculated into 5 ml of the YPD 12 L liquid medium (yeast extract 1%, peptone 2%, glucose 12%, proteolipid 1%) to a cell density of 31.6 g (on the dry cell basis)/L and fermentation was carried out at 32° C. for 9 hours. Lactic acid production after completion of the fermentation was 99.2 g/L and its sugar base yield was 83%. Strain ASP2782 was inoculated into 5 ml of the YPD 12 liquid medium (yeast extract 1%, peptone 2%, glucose 12%) to a cell density of 44.0 g (on the dry cell basis)/L and fermentation was carried out at 32° C. for 6 hours. Lactic acid production after completion of the fermentation was 85.7 g/L and its sugar base yield was 88%.

From the above results, it was shown that the strain ASP2782 from which the pdc2 gene was deleted has a productivity superior to that of the strain ASP2767 from which the pdc2 gene was not deleted.

While the present invention has been described in detail and with reference to specific embodiments thereof, it will be apparent to one skilled in the art that various changes and modifications can be made therein without departing from the spirit and scope of the present invention.

This application is based on a Japanese Patent Application No. 2009-192271 filed on Aug. 21, 2009, the entire contents of which are incorporated herein by reference. In this connection, all contents of the references cited in the specification are incorporated as references.

INDUSTRIAL APPLICABILITY

Since the transformant of the present invention and the lactic acid production method which uses the same can produce lactic acid with a high productivity without carrying out neutralization by an alkali even at a low pH, these can be used suitably as an industrial production method of lactic acid.

The invention claimed is:

1. A *Schizosaccharomyces pombe* transformant, wherein the transformant is transformed with a lactate dehydrogenase gene, wherein the chromosomal pyruvate decarboxylase (PDC) 2 gene in the transformant is deleted or inactivated, wherein the chromosomal PDC 4 gene in the transformant is not deleted or inactivated, and wherein the transformant produces lactic acid at a pH of 3.5 or less, while maintaining ethanol production suitable for growth of the transformant.

2. The transformant according to claim 1, wherein the lactate dehydrogenase gene is a mammalian lactate dehydrogenase gene.

3. The transformant according to claim 1, wherein the lactate dehydrogenase gene is inserted into the chromosome of the transformant.

4. A method for producing the transformant of claim 1, comprising:
   transforming a *Schizosaccharomyces pombe* host cell with a vector comprising an expression cassette that comprises a promoter, a terminator and a lactate dehydrogenase gene functioning in the *Schizosaccharomyces pombe* host to obtain a transformant,
   wherein a PDC 2 gene in the *Schizosaccharomyces pombe* host cell or transformant is deleted or inactivated, wherein the chromosomal PDC 4 gene in the transformant is not deleted or inactivated, and wherein the transformant produces lactic acid at a pH of 3.5 or less, while maintaining ethanol production suitable for growth of the transformant.

5. The method according to claim 4, wherein the vector further comprises a recombination region for carrying out a homologous recombination for the chromosome of the *Schizosaccharomyces pombe* host cell, and the expression cassette is inserted into a target region of the chromosome of the *Schizosaccharomyces pombe* host cell.

6. The method according to claim 5, wherein the target region where the homologous recombination is carried out in the chromosome of the host cell is a transposon gene Tf2.

7. The method according to claim 4, wherein the lactate dehydrogenase gene is a mammalian lactate dehydrogenase gene.

8. A method for producing lactic acid, which comprises culturing the transformant according to claim 1 in a culture medium and obtaining lactic acid from the culture medium.

9. The method according to claim 8, wherein the culture medium comprises from 1% by mass to 50% by mass in concentration of glucose.

10. The method according to claim 8, wherein the culturing is continued after the pH of the culture becomes 3.5 or less due to the lactic acid produced by the transformant.

11. The method according to claim 8, wherein the initial cell density of the transformant in the culture medium is from 0.1 g to 50 g/L on a dry cell basis.

12. The method according to claim 8, wherein the culturing is continued without neutralizing the lactic acid in the culture medium produced by the transformant.

13. The method according to claim 8, wherein the lactic acid is separated from the culture medium without neutralizing lactic acid in the culture produced by the transformant.

14. The transformant according to claim 1, wherein
    the lactate dehydrogenase gene is a mammalian lactate dehydrogenase gene, and
    the lactate dehydrogenase gene is inserted into the chromosome of the transformant.

* * * * *

SEQUENCE LISTING

```
<160> NUMBER OF SEQ ID NOS: 74

<210> SEQ ID NO 1
<211> LENGTH: 999
<212> TYPE: DNA
<213> ORGANISM: Homo sapiens

<400> SEQUENCE: 1
atggcaactc taaaggatca gctgatttat aatcttctaa aggaagaaca gaccccccag      60
aataagatta cagttgttgg ggttggtgct gttggcatgg cctgtgccat cagtatctta     120
atgaaggact tggcagatga acttgctctt gttgatgtca tcgaagacaa attgaaggga     180
gagatgatgg atctccaaca tggcagcctt ttccttagaa caccaaagat tgtctctggc     240
aaagactata atgtaactgc aaactccaag ctggtcatta tcacggctgg ggcacgtcag     300
caagagggag aaagccgtct taatttggtc cagcgtaacg tgaacatctt taaattcatc     360
attcctaatg ttgtaaaata cagcccgaac tgcaagttgc ttattgtttc aaatccagtg     420
gatatcttga cctacgtggc ttggaagata agtggttttc ccaaaaaccg tgttattgga     480
agcggttgca atctggattc agcccgattc cgttacctaa tgggggaaag gctgggagtt     540
cacccattaa gctgtcatgg gtgggtcctt ggggaacatg gagattccag tgtgcctgta     600
tggagtggaa tgaatgttgc tggtgtctct ctgaagactc tgcacccaga tttagggact     660
gataaagata aggaacagtg gaaagaggtt cacaagcagg tggttgagag tgcttatgag     720
gtgatcaaac tcaaaggcta cacatcctgg gctattggac tctctgtagc agatttggca     780
gagagtataa tgaagaatct taggcgggtg cacccagttt ccaccatgat taagggtctt     840
tacggaataa aggatgatgt cttccttagt gttccttgca ttttgggaca gaatggaatc     900
tcagaccttg tgaaggtgac tctgacttct gaggaagagg cccgtttgaa gaagagtgca     960
gatacacttt gggggatcca aaaggagctg caattttaa                            999

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggcaaatcg tgaactcgg                                                   19

<210> SEQ ID NO 3
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccaattcca ctctcaatag cccgaacgtt ccgtctcg                             38

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctattgaga gtggaattgg c                                               21

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agtgggattt gtagctaagc tactggtttc cacattgttt gg                        42

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagtttcgtc aatatcacaa gctcgagacg gaacgttcgg                           40

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttacaatgct gagtgtgtat tcc                                             23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgaactcggt tgaaaaatgt cg                                              22

<210> SEQ ID NO 9
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
tgagtgtgta ttccttttc gc                                           22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctctccagct ccatccataa g                                            21

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gacacaactt cctaccaaaa agcctttctg cccatgtttt ctgtc                  45

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 gcttttggt aggaagttgt gtc                                           23

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agtgggattt gtagctaagc tgtatccatt tcagccgttt gtg                    43

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagtttcgtc aatatcacaa gctgacagaa acatgggca gaaag                   45

<210> SEQ ID NO 15
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 15
gttccttaga aaaagcaact ttgg                                              24

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cataagcttg ccaccacttc                                                   20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaaaaagcaa ctttggtatt ctgc                                              24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaggcatatt cgttgattaa ccc                                               23

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggtggaaagg tttgtgcaat ccgtcaactc atgatatttc tttatgg                     47

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gattgcacaa acctttccac c                                                 21

<210> SEQ ID NO 21
<211> LENGTH: 45
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 21
agtgggattt gtagctaagc tcatcccaca tctgtaataa tcacg                    45

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagtttcgtc aatatcacaa gctccataaa gaaatatcat gagttgacg                49

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tttgagaaga aaattttatg tccagc                                         26

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccatttagca gtataagggt cg                                             22

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagtaaaaat gtgaaagcaa tgtagg                                         26

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acacacaaac acttccattc c                                              21

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 27
cctaacaaaa gcatcatttg agaagacgaa tgaaatgaca gcaac          45

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttctcaaatg atgcttttgt tagg                                  24

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agtgggattt gtagctaagc tctggacaag tctaccttgg ag              42

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagtttcgtc aatatcacaa gctgttgctg tcatttcatt cgtc            44

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gatacaggag tacaacaaaa cac                                   23

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tctccatccc tcctccc                                          17

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgctactta aacaagacaa gc                                            22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcattcctcg atattcagtt c                                             21

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gccagtggga tttgtagcta ctctgatcgg catttttggg                         40

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtttcgtcaa tatcacaagc ttccccaacc tcccatttcc tcc                     43

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctacgatcag aagaagatca atgagacgcg gaaggggagc gcc                     43

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcgctcccc ttccgcgtct cattgatctt cttctgatcg tag                     43

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 39
atgcatttca ctctattcct c                                         21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gctatagtta agtgtaagac                                           20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttgtccacac cactcattcg                                           20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atcgtcgtcg atgctgattg g                                         21

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccagtggga tttgtagctc agcagtcatt ctcattccg                      39

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgtcaatatc acaagcttgt ctccccttct attgggattt gc                  42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```

```
gattacctgc aatcatgttt ccggccttttt gtgaaacctg cc                    42
```

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
ggcaggtttc acaaaaggcc ggaaacatga ttgcaggtaa tc                     42
```

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ggagaatgat gtattggtaa ataac                                        25
```

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
ccttgggaat gagcgaattc                                              20
```

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
gggttgtgaa gagcatactg                                              20
```

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
gaaggagatt atgtgaaaca agttgaaatc                                   30
```

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agcttagcta caaatcccac tctgagggta gtgttcttgc tacaaaaatc t    51

<210> SEQ ID NO 52
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aagtttcgtc aatatcacaa gctcatgacg gaagattccg agaaattccg ttt    53

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caaagccatg cttttaatgt taaagtgaat    30

<210> SEQ ID NO 54
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
attcacttta acattaaaag catggctttg atcgattgag atttttgtag caagaacact    60

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggaaatggtt catgtggact gggttttatt    30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctgctctta aaatgacgaa tggtgtaggc    30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atatagtgcg atatggatga aggagaagag    30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atcataactt actatatcgt gaagaagaga                                    30

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agcttagcta caaatcccac ttagaatgag taattcaact tcttaaacca c            51

<210> SEQ ID NO 60
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aagtttcgtc aatatcacaa gctttagctt aaaagtaata agcttctatg tga          53

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgaagacatt ttataaaact taaataaaaa                                    30

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tttttattta agttttataa aatgtcttca gaaatttaaa tctgtggttt aagaagttga   60

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
actttgttta ttgtagaaag tcgagcttga                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
caaaagacag gggtcggatt gattccttgg                                      30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgtgctgttt ttcaagtggt catgcgttac                                      30

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agcttagcta caaatcccac t                                               21

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agcttgtgat attgacgaaa ctt                                             23

<210> SEQ ID NO 68
<211> LENGTH: 5558
<212> TYPE: DNA
<213> ORGANISM: Homo sapiens

<400> SEQUENCE: 68
actagtgaat tcgagtatgt gtacgagttg tctttaaacc cacagaggta gaatgtatat     60
ataaaattaa taagctaagt gtaatactta aaaaatacat taattggaac tcgtatccta    120
ccatttacaa tgttcatcca attttttcag attgtactgt aaatagcgtt tgaaaacacc    180 aaatttttaga agctaatcac tctcatcata atcgtctaca tcctcatcgt tatcgacgat    240
aaaagaatca tcttgcatgc tgggttcatc catgctatca aacgagggat caacgtaaat    300
aggtgttttc actgtagccg ctgctcttct ggttggcctc tttctaatcg gagaatctga    360
atcttctggt ggctctgcgt tagtcgaact agcttttgga gttgaactac tacctggaat    420
aataaaatca tcatcgtcat cttcaggtga ttgtttcttt accgagcttg cttttttccc    480
tttattcttc gcagaagcct tcgtggatgt tatggtggaa ggtttcaaac tgctaggcaa    540
caaatcatct tcatcgtctg aagaaaatat ggtagtagca actggtttat tagtcttttct   600

```
tcctcttcca gacgccgagg ctgctatttt ttttgacgggt tttttactac ctgcgtcttc      660
agagtcaaca gattgacttc tttttcttga ttttccacta tcactgctat ccaatcccgg      720
gctcttagat atgcgatttt cttcaactga taagccatga gagttatcct ctgtcttgac      780
aatgtttatg tcagatgatt tctcaggttc tttcgacgct gcgaactcaa gtaaagtttg      840
ttgctttcga tttgttgtag atggtttgga ttcgctgcta gcttcttttt taacagcagt      900
acttgaggag gatccggcaa tagccctggg tttcctagta ccagtggatt tacctcgagg      960 cttcttttt cgttcgattta caaaatctct tgaggattgc tcttcttcta acatttctct     1020
ctgaatatca tccataacct tattccaagc atgctcaaat gcatccaaat catgaagcca     1080
caattcttta ggagttttt taatcaaagc atccagttcg gccattactt cgtccttttt     1140
cttgagaagt tccacatacc gttcataggt caaagaccat aaaggcattg aaagaaggta     1200
attgtaggca tctgaatcct cgtcttgcga acatcacca gattgttctt cttcagcaag     1260 agcatttca acttctaaat caaccaaatg ccctttcttt ggtttactga taggttgaaa     1320
cttcttttcc ttcagctcca caatgagatc ttttttcttc tttttgaaa ctacaagctc      1380 cccctctata atcatatgaa taaaccgcgc ttgatttgaa atctatcaa acctttttc       1440 caattcatta accatatgct ctttacgtct ctggtatgtc cttaaacgta cttcgtaaaa     1500
ctcggtcaaa atatcttcaa cactgtcata cttcttgatc cgtccagatg catcaaaagc     1560
aatcatatta ctcgttgctt gagtacgcga cagtttaaac ttaacttcca aggattcatt     1620
taatgcttct ttcatgccag cttcggtaag cgtgacatta aagtgaacat ttccttcacc     1680
gtgatggctt tcatagtcca cgatgaattt acgaattttt tccgtaccaa caagaccagc     1740
ctccagatac tccttcattc gtacgtggct taactatgcg gcatcagagc agattgtact     1800
gagagtgcac catatgcggt gtgaaatacc gcacagatgc gtaaggagaa ataccgcat     1860 caggcgctct tccgcttcct cgctcactga ctcgctgcgc tcggtcgttc ggctgcggcg     1920
agcggtatca gctcactcaa aggcggtaat acggttatcc acagaatcag gggataacgc     1980
aggaaagaac atgcatgtga gcaaaaggcc agcaaaaggc caggaaccgt aaaaaggccg     2040
cgttgctggc gtttttccat aggctccgcc cccctgacga gcatcacaaa aatcgacgct     2100
caagtcagag gtggcgaaac ccgacaggac tataaagata ccaggcgttt ccccctggaa     2160
gctccctcgt gcgctctcct gttccgaccc tgccgcttac cggatacctg tccgcctttc     2220
tcccttcggg aagcgtggcg ctttctcata gctcacgctg taggtatctc agttcggtgt     2280
aggtcgttcg ctccaagctg ggctgtgtgc acgaaccccc cgttcagccc gaccgctgcg     2340
ccttatccgg taactatcgt cttgagtcca acccggtaag acacgactta tcgccactgg     2400
cagcagccac tggtaacagg attagcagag cgaggtatgt aggcggtgct acagagttct     2460
tgaagtggtg gcctaactac ggctacacta aaggacagt atttggtatc tgcgctctgc     2520
tgaagccagt taccttcgga aaagagttg gtagctcttg atccggcaaa caaccaccg      2580 ctggtagcgg tggtttttt gtttgcaagc agcagattac gcgcagaaaa aaggatctc      2640 aagaagatcc tttgatcttt tctacggggt ctgacgctca gtggaacgaa aactcacgtt     2700
aagggatttt ggtcatgaga ttatcaaaaa ggatcttcac ctagatcctt ttaaattaaa     2760
aatgaagttt taaatcaatc taaagtatat atgagtaaac ttggtctgac agttaccaat     2820
gcttaatcag tgaggcacct atctcagcga tctgtctatt tcgttcatcc atagttgcct     2880
gactccccgt cgtgtagata actacgatac gggagggctt accatctggc cccagtgctg     2940
```

```
caatgatacc gcgagaccca cgctcaccgg ctccagattt atcagcaata aaccagccag    3000
ccggaagggc cgagcgcaga agtggtcctg caactttatc cgcctccatc cagtctatta    3060
attgttgccg ggaagctaga gtaagtagtt cgccagttaa tagtttgcgc aacgttgttg    3120
ccattgctgc aggcatcgtg gtgtcacgct cgtcgtttgg tatggcttca ttcagctccg    3180
gttcccaacg atcaaggcga gttacatgat cccccatgtt gtgcaaaaaa gcggttagct    3240
ccttcggtcc tccgatcgtt gtcagaagta agttggccgc agtgttatca ctcatggtta    3300
tggcagcact gcataattct cttactgtca tgccatccgt aagatgcttt tctgtgactg    3360
gtgagtactc aaccagtca ttctgagaat agtgtatgcg cgaccgagt tgctcttgcc    3420 cggcgtcaac acgggataat accgcgccac atagcagaac tttaaaagtg ctcatcattg    3480
gaaaacgttc ttcggggcga aaactctcaa ggatcttacc gctgttgaga tccagttcga    3540
tgtaacccac tcgtgcaccc aactgatctt cagcatcttt tactttcacc agcgtttctg    3600
ggtgagcaaa aacaggaagg caaaatgccg caaaaaaggg aataagggcg acacggaaat    3660
gttgaatact catactcttc cttttcaat attattgaag catttatcag ggttattgtc    3720
tcatgagcgg atacatattt gaatgtattt agaaaaataa acaaataggg gttccgcgca    3780
catttccccg aaaagtgcca cctgacgtct aagaaaccat tattatcatg acattaacct    3840
ataaaaatag gcgtatcacg aggccctttc gtcttcaaga attgttgttc gtacggcggc    3900
ttcgatagct tcagcctcct taggagcatt caaaccataa cgaaggagaa gggaagcaga    3960
taaaattgta ccaacaggat taacaatgcc cttgccagcg atatcgggag cgctaccgtg    4020
aatgggctca accaaacaat gaaccttttc ttctgatttt cctaccacac cggaaaggga    4080
ggcagaaggc aaaaggccca agctaccagg aatgacagaa gcctcatctg aaataatgtc    4140
accaaacaag ttgtcagtca aaacaacacc gttaagtgta cgagggctct tgaccaaaag    4200
catggctgcg gagtcaatga gctggttttt taaggtaagg tgaggatatt cctccttaaa    4260
aatcttagct acagtcttgc gccaaagacg agaagttgcc aaaacattag ctttgtcgag    4320
taatgtgacg ggagcaggag ggttggaagt ttcagctaac caagcagcca aacgagcaat    4380
acgagaaact tcttccaaac tgtaaggcca agtgtccata gcataaccg atccgttgtc    4440 ctcagtgcgc tcaccaaagt aacaacctcc agtaagttct cgtacaacac aaaaatcgac    4500
accttcaacg atttcaggct tcaaagggct gtacttgact aaagacttgc tggcaaagtt    4560
gcaaggtcga aggttggccc aaacacccat actcttacga agcttcaata aaccttgctc    4620
aggacgacaa ttgggggttgg tccattcagg accaccaacg gcacccaaaa gaacaccgtc    4680
agcttccaaa caagccttca cagtctcgtc agtcaaaggg gttccatagg catcaataga    4740
ggcacctcca atcttgtgtt cttcaaactc gagtttaac tcaggtcgct tcttctcaac    4800
gactttcaaa acctccaagg cagaagcaac aatttcaggg ccaatatggt ctcctggtaa    4860
gacgacgatt ttcttttgcac acatgttgtt gaagaagttt tgttgtgaaa tggtttcgtg    4920
aaagtttcag accctaccgc aaaaatgcct ggtttcggga aactcaacac tgttgcactt    4980
tttatactac agattgggat atcgataata ttgcgtaaaa aatcctttt ttaaaaagct    5040 tgtttacagt aacgtaaatg accagaaatc agatgaaaat cacaagaaag caataattc    5100 acgttaaatc ctgatatgtt tgattttgtg atgaaatcat ggatgttcat aggaattgtt    5160
gaaattgcgc ttttttaacg aaatatacaa gtatcctgga gcttacttaa ttaattaatg    5220
aatctttgtt tctagatatt aaaatagtag cctcaattat cagcgctttc tacgttagta    5280
aacgaaattt ttaatgtcaa aaaaatgttt aatagacagt acgaatatgc attataatgt    5340
```

-continued

```
tcataaataa tttgagtatg tgtacgagtt gtctttaaac ccacagaggt agaatgtata    5400
tataaaatta ataagctaag tgtaatactt aaaaaataca ttaattggaa ctcgtatcct    5460
accatttaca atgttcatcc aatttttca gattgtactg taaatagcgt ttgaaaacac     5520
caaattttag aagctaatca ctctcatcat aatcgtct                            5558
```

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
gtccatggca actctaaagg atcag                                            25
```

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
cagtcgactt aaaattgcag ctccttttg                                        29
```

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
aaggcctcgt acgtgaaagc aagagcaaaa cga                                   33
```

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
aaggcctcgt acgtgctttg tccgcttgta gc                                    32
```

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
ggggtaccaa gcttctagag tcgactccgg tgctacgaca cttt                       44
```

<210> SEQ ID NO 74
<211> LENGTH: 45
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 74
ggggtaccag gcctctcgag gctagccatt tccagcgtac atcct                              45
```